(12) United States Patent
Tokuda et al.

(10) Patent No.: US 9,993,211 B2
(45) Date of Patent: Jun. 12, 2018

(54) SYSTEM AND METHOD FOR AUTOMATIC DETECTION AND REGISTRATION OF MEDICAL IMAGES

(71) Applicants: Junichi Tokuda, Newton, MA (US); Sang-Eun Song, Chestnut Hill, MA (US); Nobuhiko Hata, Waban, MA (US)

(72) Inventors: Junichi Tokuda, Newton, MA (US); Sang-Eun Song, Chestnut Hill, MA (US); Nobuhiko Hata, Waban, MA (US)

(73) Assignee: The Brigham and Women's Hospital, Inc., Boston, MA (US)

( * ) Notice: Subject to any disclaimer, the term of this patent is extended or adjusted under 35 U.S.C. 154(b) by 487 days.

(21) Appl. No.: 14/491,872

(22) Filed: Sep. 19, 2014

(65) Prior Publication Data
US 2015/0087965 A1 Mar. 26, 2015

Related U.S. Application Data

(60) Provisional application No. 61/880,520, filed on Sep. 20, 2013.

(51) Int. Cl.
*G06T 7/00* (2017.01)
*A61B 6/03* (2006.01)
(Continued)

(52) U.S. Cl.
CPC ............ *A61B 6/032* (2013.01); *A61B 6/5211* (2013.01); *A61B 34/10* (2016.02); *A61B 90/37* (2016.02); *G06T 3/0068* (2013.01); *G06T 7/344* (2017.01); *A61B 5/055* (2013.01); *A61B 2090/3983* (2016.02); *A61B 2576/00* (2013.01); *G06T 2207/10072* (2013.01); *G06T 2207/30081* (2013.01)

(58) Field of Classification Search
CPC ........ A61B 2090/3983; A61B 2576/00; A61B 34/10; A61B 5/005; A61B 6/032
See application file for complete search history.

(56) References Cited

U.S. PATENT DOCUMENTS

| | | | |
|---|---|---|---|
| 2011/0313285 A1* | 12/2011 | Fallavollita | A61B 6/4441 600/426 |
| 2013/0172731 A1* | 7/2013 | Gole | A61B 5/0035 600/424 |
| 2014/0107569 A1* | 4/2014 | Fischer | A61M 5/3287 604/95.01 |

OTHER PUBLICATIONS

Y. Sato et al; "Three-dimensional multi-scale line filter for segmentation and visualization of curvilinear structures in medical images;" Medical Image Analysis; 1998; pp. 143-168.

(Continued)

*Primary Examiner* — Baisakhi Roy
(74) *Attorney, Agent, or Firm* — Quarles & Brady LLP

(57) ABSTRACT

A system and method for automatic registration of medical images includes accessing image data of a subject and plurality of elongated fiducial markers arranged in an asymmetrical orientation and analyzing the image data to detect the elongated fiducial markers by applying a line filter to treat the elongated fiducial markers as lines within the image data. The system and method also includes matching the elongated fiducial markers within the image data to a model of the elongated fiducial markers, registering the image data with a coordinate system based on the matching, and generating a report indicating at least the registered image data.

20 Claims, 6 Drawing Sheets

(51) Int. Cl.
*G06T 3/00* (2006.01)
*A61B 6/00* (2006.01)
*A61B 34/10* (2016.01)
*G06T 7/33* (2017.01)
*A61B 5/055* (2006.01)
*A61B 90/00* (2016.01)

(56) References Cited

OTHER PUBLICATIONS

Majd Alshawa; "ICL : Iterative closest line—A novel point cloud registration algorithm based on linear features;" 2007; pp. 53-59.

* cited by examiner

SYSTEM AND METHOD FOR AUTOMATIC DETECTION AND REGISTRATION OF MEDICAL IMAGES

CROSS-REFERENCE TO RELATED APPLICATIONS

This application is based on, claims priority to, and incorporates herein by reference in its entirety for all purposes U.S. Provisional Patent Application Ser. No. 61/880,520, filed Sep. 20, 2013, and entitled "SYSTEM AND METHOD FOR AUTOMATIC DETECTION AND REGISTRATION OF MEDICAL IMAGES."

STATEMENT REGARDING FEDERALLY SPONSORED RESEARCH

This invention was made with Government support under Grant Numbers CA111288, CA138486 and EB014898 awarded by the National Institutes of Health. The Government has certain rights in this invention.

BACKGROUND

The present disclosure relates generally to systems and methods for medical imaging and, more particularly, the disclosure relates to systems and methods for automated detection and registration of medical images using advantageously correlated fiducial markers and processing algorithms.

Fiducial markers are used regularly in a wide variety of medical procedures. For example, fiducial markers are used to provide a point of reference on a patient during many surgical and therapeutic procedures, such as radiotherapy and radio surgery and medical imaging procedures.

For example, Magnetic resonance imaging (MRI) is an advantageous option as an intra-operative imaging modality for image-guided prostate interventions. While transrectal ultrasound (TRUS) is the most commonly used imaging modality to guide core needle prostate biopsy in the United States, the limited negative predictive value of the TRUS-guided systematic biopsy has been argued. To take advantage of MRI's excellent soft tissue contrast, researchers have been investigating the clinical utility of MRI for guiding targeted biopsies. MRI-guided prostate biopsies are often assisted by needle guide devices or MRI-compatible manipulators. These devices allow the radiologist to insert a biopsy needle accurately into the target defined within the MRI coordinate space.

Within this context, registering needle guide devices to the MRI coordinate system is essential for accurate needle placement. These devices are often equipped with MR-visible passive markers to be localized in the MRI coordinate system. Because the locations of those markers in the device's own coordinate system are known, one can register the device's coordinate system to the MRI coordinate system by detecting the markers on an MR image. However, the detection and registration of markers on an MR image are not always simple to achieve, because simple thresholding does not always provide robust automatic detection due to noise from other sources such as the patient's anatomy. Even if the markers are successfully detected, associating them with the individual markers is another hurdle for device-to-image registration. Existing methods rely on specific designs of fiducial frames or MR sequences, restricting the device design.

Stereotactic radiosurgery procedures often employ a physical stereotactic frame to the patient's skull to serve as a Cartesian reference. Several frames have been developed for this purpose, including the Leksell frame, Brown-Roberts-Wells ("BRW") frame, and Fisher frame, among others. To guide the procedure, in imaging process, such as digital subtraction angiography ("DSA") is often employed. During angiography a localizer box is attached to the frame and two-dimensional images of the patient are obtained, in which the target area for therapy can be readily identified. The two-dimensional projected target area in the DSA images is transferred to the stereotactic frame's three-dimensional coordinate system. During subsequent computed tomography ("CT") imaging, a CT localization device is attached to the stereotactic frame, so that the obtained CT images are correlated to the stereotactic frame. During radiation treatment, the frame is attached to a stand such that the target of the therapy is accurately placed in the isocenter of the treatment system. The technique allows for precise radiation treatment; however, the use of the frame and use of the CT localization device and the need to accurately register multiple imaging and therapy modalities can be quite cumbersome.

An image-guided photon radiosurgery system, such as the CyberKnife® system manufactured by Accuray, Inc. (Sunnyvale, Calif.), is said to be a so-called "frameless" system. With a frameless, image-guided system, the invasive stereotactic frame and attached localizer box are no longer needed either during CT imaging, or radiation treatment of the patient. For brain diseases, the target treatment area can be determined on CT images, which may be fused with images obtained with other imaging modalities. To do so, imaging registration is performed using anatomical structures and fiducial markers in both images. By comparing these two-dimensional images, information regarding the translations and rotations necessary to align the two images can be determined; however, the process can be quite painstaking, as automated methods can be error prone.

For proton and heavy charged particle treatment, it is highly desirable to reduce the number of devices that intersect the treatment beam trajectory to a minimum in order to minimize unwanted attenuation of the treatment beam. In these frameless setups, for stereotactic treatment of patients, at least three small fiducials are implanted into the patient's skull, after which, positioning is guided by digitized orthogonal skull radiographs that depict the fiducials.

The frameless, image-guided approach is comfortable for the patient, and multi-fraction treatment can be routinely performed using this treatment planning approach. However, without the stereotactic frame, image registration can be very difficult and relies on anatomical markers and any fiducial markers that are employed.

Despite the fact that fiducial markers are an integral tool used to facilitate, automated methods for registering images or assisting in therapeutic planning using the fiducial markers can still be limited and error prone. It would therefore be desirable to provide a system and method for automating image analysis and image registration that does not suffer from the drawbacks described above.

SUMMARY

The present disclosure overcomes the aforementioned drawbacks by providing a system and method for automatically processing medical images that include elongated fiducial markers arranged asymmetrically. The automated processing regards the elongated fiducial markers as lines that are enhanced using a multi-scale line filter. An iterative processing is performed to match the enhanced lines to a model of a fiducial frame.

Thus, in accordance with one aspect of the disclosure, a system is disclosed that includes a computer system including a non-transitive, computer-readable storage medium having stored thereon a program that causes the computer system to access image data of a subject and plurality of elongated fiducial markers arranged in an asymmetrical orientation. The computer system is further caused to analyze the image data to detect the elongated fiducial markers by applying a line filter to treat the elongated fiducial markers as lines within the image data, enhance a contrast of the elongated fiducial markers within the image data, and match the enhanced contrast of the elongated fiducial markers within the image data to a model of the elongated fiducial markers. The computer system is also caused to register the image data with a coordinate system based on the matching of the enhanced contrast of the elongated fiducial markers to the model of the elongated fiducial markers and generate a report indicating at least the registered image data.

In accordance with another aspect of the disclosure, a method for automatically registering medical images with an image coordinate system is disclosed. The method includes arranging a fiducial frame having a plurality of elongated fiducial markers arranged asymmetrically proximate to a subject, acquiring, with a medical imaging system, image data of the subject and fiducial frame, and applying a line filter that treats the elongated fiducial markers as lines within the image data. The method also includes distinguishing the elongated fiducial markers within the image data and matching the elongated fiducial markers within the image data to a model of the elongated fiducial markers. The method further includes registering the image data with a coordinate system based on the matching of the elongated fiducial markers to the model of the elongated fiducial markers and generating a report indicating at least the registered image data.

In accordance with yet another aspect of the disclosure, a system for automatically registering medical images with an image coordinate system is disclosed. The system includes a fiducial frame having a plurality of elongated fiducial markers arranged asymmetrically within the fiducial frame and an imaging system configured to acquire image data from the fiducial frame and a subject located proximate to the fiducial frame. A computer system is included that has a non-transitive, computer-readable storage medium having stored thereon a program that causes the computer system to access the image data of the subject and the fiducial frame. The computer system is also caused to analyze the image data to detect the elongated fiducial markers by applying a line filter to treat the elongated fiducial markers as lines within the image data and match the elongated fiducial markers detected within the image data to a model of the elongated fiducial markers. The computer system is further caused to register the image data with a coordinate system based on the matching of the enhanced contrast of the elongated fiducial markers to the model of the elongated fiducial markers and generate a report indicating at least the registered image data.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION

As will be described, the present disclosure provides a system and method for robust automatic fiducial frame detection and registration that can be applied to a variety of fiducial frame designs and/or imaging or therapy modalities. The fiducial frame design may include at least three elongated or cylindrical markers that are arranged asymmetrically arranged. The resulting images are processed to extract linear features from the elongated markers using a line filter. An iterative processing is performed to match the extracted features to a model. The result is a automated image analysis and/or registration that is more robust than that of traditional methods that, for example, rely on bright spots on the image by to be matched using a thresholding criteria. By matching the elongated shapes detected on an image and a model of the fiducial frame, one can register the frame to the coordinate system of the imaging modality, a surgical modality, a therapy modality, or other system.

Figure 1:
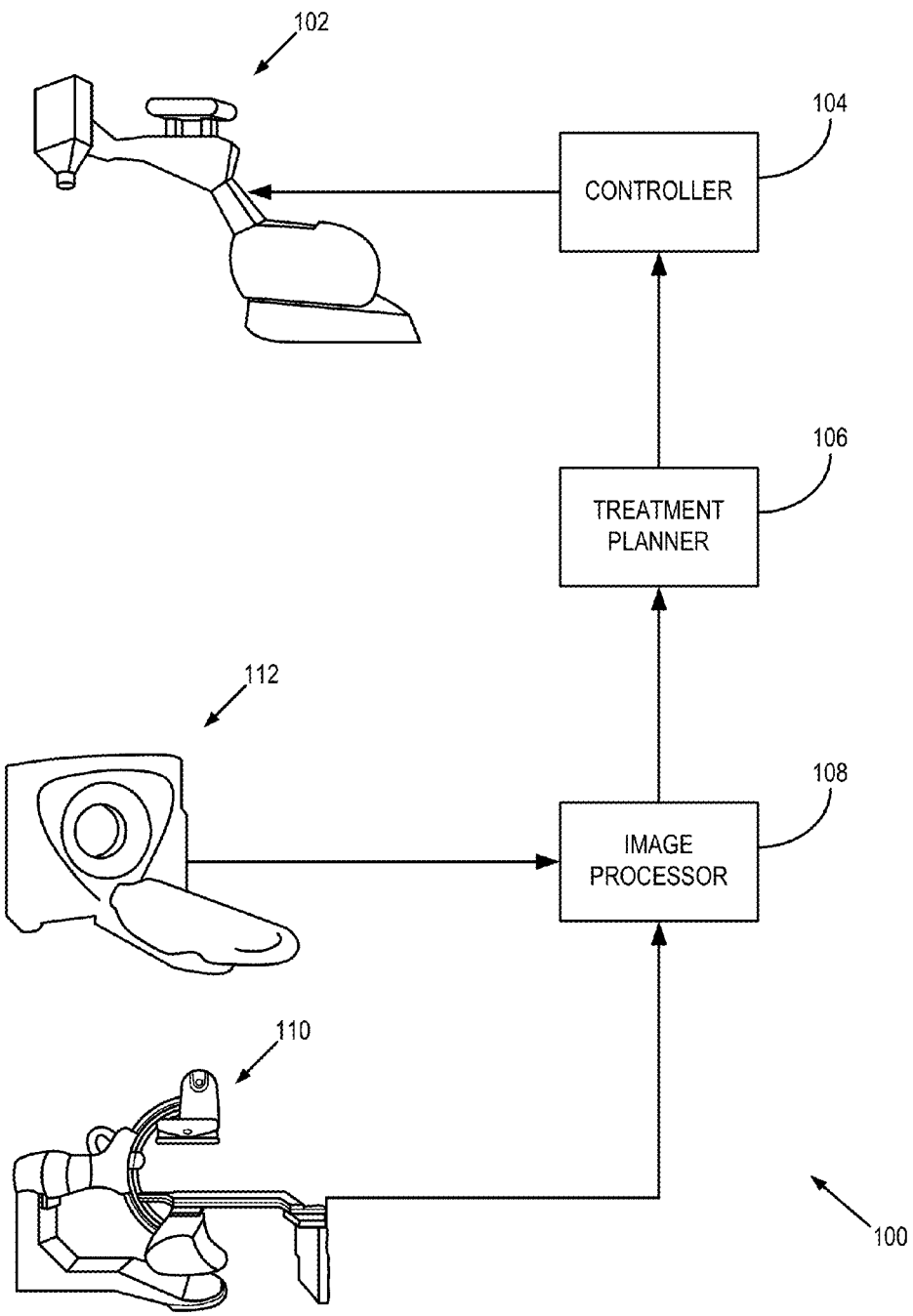
FIG. 1 is a schematic diagram of an exemplary stereotactic radiation surgery system including the stereotactic radiosurgery apparatus for use with the present disclosure.

Referring to FIG. 1, a block diagram of an exemplary stereotactic radiosurgery system ("SRS") 100 is illustrated. The SRS 100 includes a stereotactic radiosurgery apparatus 102 that is controlled by controller 104 such that a radiation dose is delivered to a patient with high accuracy. Exemplary stereotactic radiosurgery apparatus include CyberKnife® systems manufactured by Accuray Inc. (Sunnvale, Calif.); Gamma Knife® systems manufactured by Elekta AB (Stockholm, Sweden); and image-guided radiotherapy ("IGRT") systems such as the Novalis Tx™ stereotactic linear accelerator ("LINAC") systems manufactured by Varian Medical Systems, Inc. (Palo Alto, Calif.); and proton and heavy charged particle treatment systems. The controller 104 receives a treatment plan from a treatment planner 106. An operator, such as a physician or medical physicist, interacts with the treatment planner 106 to produce an appropriate treatment plan that will effectively deliver radiation to the patient. The treatment planner 106 receives image data from an image processor 108, which receives images from one or more imaging systems. For example, the image processor may receive images from an x-ray imaging system 110 and an x-ray computed tomography ("CT") imaging system 112.

A general procedure for producing a stereotactic surgical or radiation treatment plan for the treatment of an arteriovenous malformation is as follows. First, a patient has fiducial markers ("fiducials"), such as temporary fiducials or implanted fiducials, affixed to their skull. The patient is then positioned within an x-ray imaging system 110, and a series of radiographs of the patient are acquired as a contrast agent is administered to the patient and allowed to pass through the patient's vasculature. Included in this series of radiographs are acquired before the administration of the contrast agent. These so-called "mask images" are used to produce a series of patient angiograms using digital subtraction angiography ("DSA") techniques. From the series of angiograms, a pair of DSA images that best depict an AVM is selected. After the patient is removed from the x-ray imaging system, and without adjusting the source-detector settings, a localizer box is imaged with the x-ray imaging system 110 such that two orthogonal radiographs of the localizer box are produced. CT images of the patient are additionally acquired with an x-ray CT imaging system 112, either before or after acquisition of the angiograph. Other images of the patient can subsequently be acquired with different imaging modalities or can be substituted for those described above, such as magnetic resonance imaging ("MRI") and these other images fused with the image volume during treatment planning.

Figure 2:
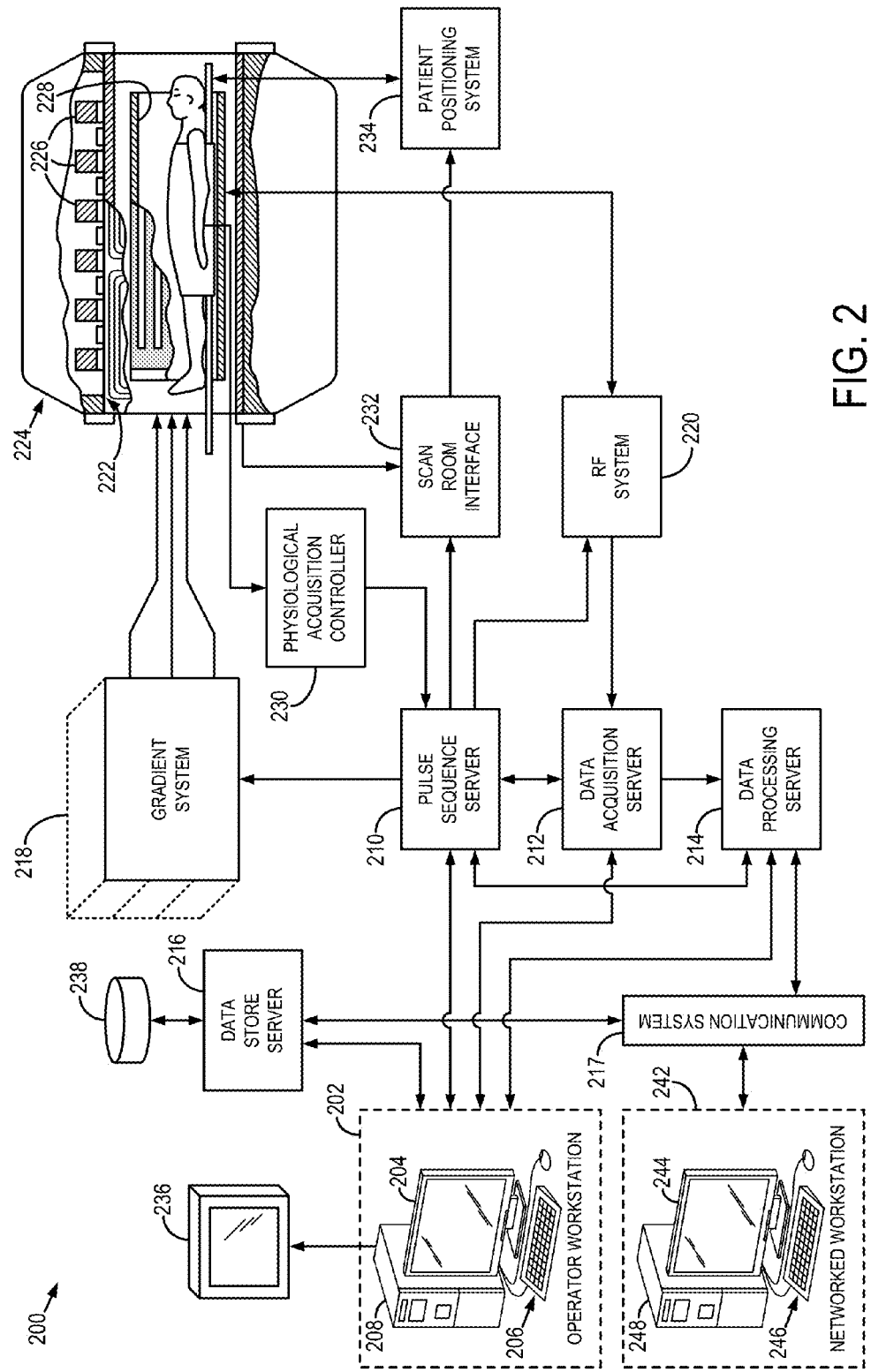
FIG. 2 is a block diagram of an example of a magnetic resonance imaging ("MRI") system for use with the present disclosure.

Specifically, referring to FIG. 2, an example of an MRI system 200 is illustrated. The MRI system 200 includes an operator workstation 202, which will typically include a display 204, one or more input devices 206, such as a keyboard and mouse, and a processor 208. The processor 208 may include a commercially available programmable machine running a commercially available operating system. The operator workstation 202 provides the operator interface that enables scan prescriptions to be entered into the MRI system 200. In general, the operator workstation 202 may be coupled to four servers: a pulse sequence server 210; a data acquisition server 212; a data processing server 214; and a data store server 216. The operator workstation 202 and each server 210, 212, 214, and 216 are connected to communicate with each other. For example, the servers 210, 212, 214, and 216 may be connected via a communication system 217, which may include any suitable network connection, whether wired, wireless, or a combination of both. As an example, the communication system 217 may include both proprietary or dedicated networks, as well as open networks, such as the internet.

The pulse sequence server 210 functions in response to instructions downloaded from the operator workstation 202 to operate a gradient system 218 and a radiofrequency ("RF") system 220. Gradient waveforms necessary to perform the prescribed scan are produced and applied to the gradient system 218, which excites gradient coils in an assembly 222 to produce the magnetic field gradients and used for position encoding magnetic resonance signals. The gradient coil assembly 222 forms part of a magnet assembly 224 that includes a polarizing magnet 226 and a whole-body RF coil 228.

RF waveforms are applied by the RF system 220 to the RF coil 228, or a separate local coil (not shown in FIG. 2), in order to perform the prescribed magnetic resonance pulse sequence. Responsive magnetic resonance signals detected by the RF coil 228, or a separate local coil (not shown in FIG. 2), are received by the RF system 220, where they are amplified, demodulated, filtered, and digitized under direction of commands produced by the pulse sequence server 210. The RF system 220 includes an RF transmitter for producing a wide variety of RF pulses used in MRI pulse sequences. The RF transmitter is responsive to the scan prescription and direction from the pulse sequence server 210 to produce RF pulses of the desired frequency, phase, and pulse amplitude waveform. The generated RF pulses may be applied to the whole-body RF coil 228 or to one or more local coils or coil arrays (not shown in FIG. 2).

The RF system 220 also includes one or more RF receiver channels. Each RF receiver channel includes an RF preamplifier that amplifies the magnetic resonance signal received by the coil 228 to which it is connected, and a detector that detects and digitizes the quadrature components of the received magnetic resonance signal. The magnitude of the received magnetic resonance signal may, therefore, be determined at any sampled point by the square root of the sum of the squares of the and components:

$$M = \sqrt{I^2 + Q^2} \qquad \text{Eqn. (1);}$$

and the phase of the received magnetic resonance signal may also be determined according to the following relationship:

$$\varphi = \tan^{-1}\left(\frac{Q}{I}\right). \qquad \text{Eqn. (2)}$$

The pulse sequence server 210 also optionally receives patient data from a physiological acquisition controller 230. By way of example, the physiological acquisition controller 230 may receive signals from a number of different sensors connected to the patient, such as electrocardiograph ("ECG") signals from electrodes, or respiratory signals from respiratory bellows or other respiratory monitoring device. Such signals are typically used by the pulse sequence server 210 to synchronize, or "gate," the performance of the scan with the subject's heart beat or respiration.

The pulse sequence server 210 also connects to a scan room interface circuit 232 that receives signals from various sensors associated with the condition of the patient and the magnet system. It is also through the scan room interface circuit 232 that a patient positioning system 234 receives commands to move the patient to desired positions during the scan.

The digitized magnetic resonance signal samples produced by the RF system 220 are received by the data acquisition server 212. The data acquisition server 212 operates in response to instructions downloaded from the operator workstation 202 to receive the real-time magnetic resonance data and provide buffer storage, such that no data is lost by data overrun. In some scans, the data acquisition server 212 does little more than pass the acquired magnetic resonance data to the data processor server 214. However, in scans that require information derived from acquired magnetic resonance data to control the further performance of the scan, the data acquisition server 212 is programmed to produce such information and convey it to the pulse sequence server 210. For example, during prescans, magnetic resonance data is acquired and used to calibrate the pulse sequence performed by the pulse sequence server 210. As another example, navigator signals may be acquired and used to adjust the operating parameters of the RF system 220 or the gradient system 218, or to control the view order in which k-space is sampled. In still another example, the data acquisition server 212 may also be employed to process magnetic resonance signals used to detect the arrival of a contrast agent in a magnetic resonance angiography (MRA) scan. By way of example, the data acquisition server 212 acquires magnetic resonance data and processes it in real-time to produce information that is used to control the scan.

The data processing server 214 receives magnetic resonance data from the data acquisition server 212 and processes it in accordance with instructions downloaded from the operator workstation 202. Such processing may, for example, include one or more of the following: reconstructing two-dimensional or three-dimensional images by performing a Fourier transformation of raw k-space data; performing other image reconstruction algorithms, such as iterative or backprojection reconstruction algorithms; applying filters to raw k-space data or to reconstructed images; generating functional magnetic resonance images; calculating motion or flow images; and so on.

Images reconstructed by the data processing server 214 are conveyed back to the operator workstation 202 where they are stored. Real-time images are stored in a data base memory cache (not shown in FIG. 2), from which they may be output to operator display 212 or a display 236 that is located near the magnet assembly 224 for use by attending physicians. Batch mode images or selected real time images are stored in a host database on disc storage 238. When such images have been reconstructed and transferred to storage, the data processing server 214 notifies the data store server 216 on the operator workstation 202. The operator workstation 202 may be used by an operator to archive the images, produce films, or send the images via a network to other facilities.

The MRI system 200 may also include one or more networked workstations 242. By way of example, a networked workstation 242 may include a display 244; one or more input devices 246, such as a keyboard and mouse; and a processor 248. The networked workstation 242 may be located within the same facility as the operator workstation 202, or in a different facility, such as a different healthcare institution or clinic.

The networked workstation 242, whether within the same facility or in a different facility as the operator workstation 202, may gain remote access to the data processing server 214 or data store server 216 via the communication system 217. Accordingly, multiple networked workstations 242 may have access to the data processing server 214 and the data store server 216. In this manner, magnetic resonance data, reconstructed images, or other data may exchanged between the data processing server 214 or the data store server 216 and the networked workstations 242, such that the data or images may be remotely processed by a networked workstation 242. This data may be exchanged in any suitable format, such as in accordance with the transmission control protocol (TCP), the internet protocol (IP), or other known or suitable protocols.

The following discussion will provide an example of a system and method in accordance with the present disclosure with reference to MR images. Of course, the images from any of a variety of other imaging modalities or applications can be substituted or supplemented. For example, the systems described above with respect to FIG. 1 or other imaging systems can likewise be used instead of MR images. Thus, the following discussion will focus on the detection of a fiducial frame formed of multiple MR-visible elongated markers from an MR image and the registration of a model of the fiducial frame to the detected markers. However, one of ordinary skill in the art will readily recognize that the description likewise applies to other imaging modalities, such as CT imaging, and can be readily combined with or applied to a variety of applications, such SRS and other surgical and therapeutic situations.

Figure 3:
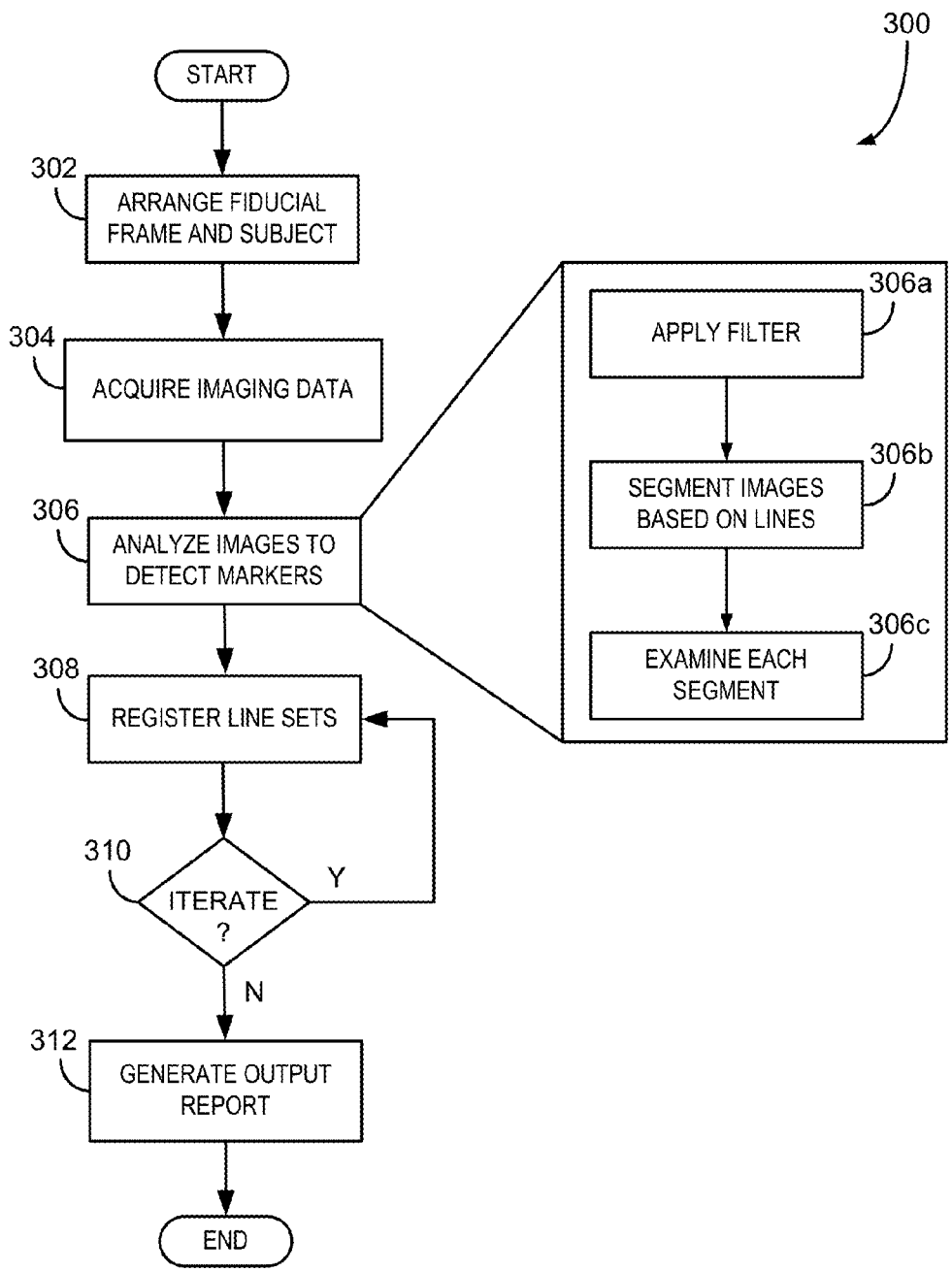
FIG. 3 is a flow chart setting forth the steps of an example process for automatic image processing in accordance with one aspect of the present disclosure.

Referring to FIG. 3, the steps 300 of a process in accordance with the present disclosure begins at process block 302 with arranging the fiducial frame relative to the subject and the imaging system. In the context of an MR imaging process, the fiducial markers can be an MR skin marker product, or sealed tubes filled with liquid that produce MR signal. Regardless of the particular construct of the markers, the arrangement of the markers frame should, preferably, be rotationally asymmetric to obtain a unique solution in marker registration, particularly in three-dimensions, as will be described.

Figure 5:
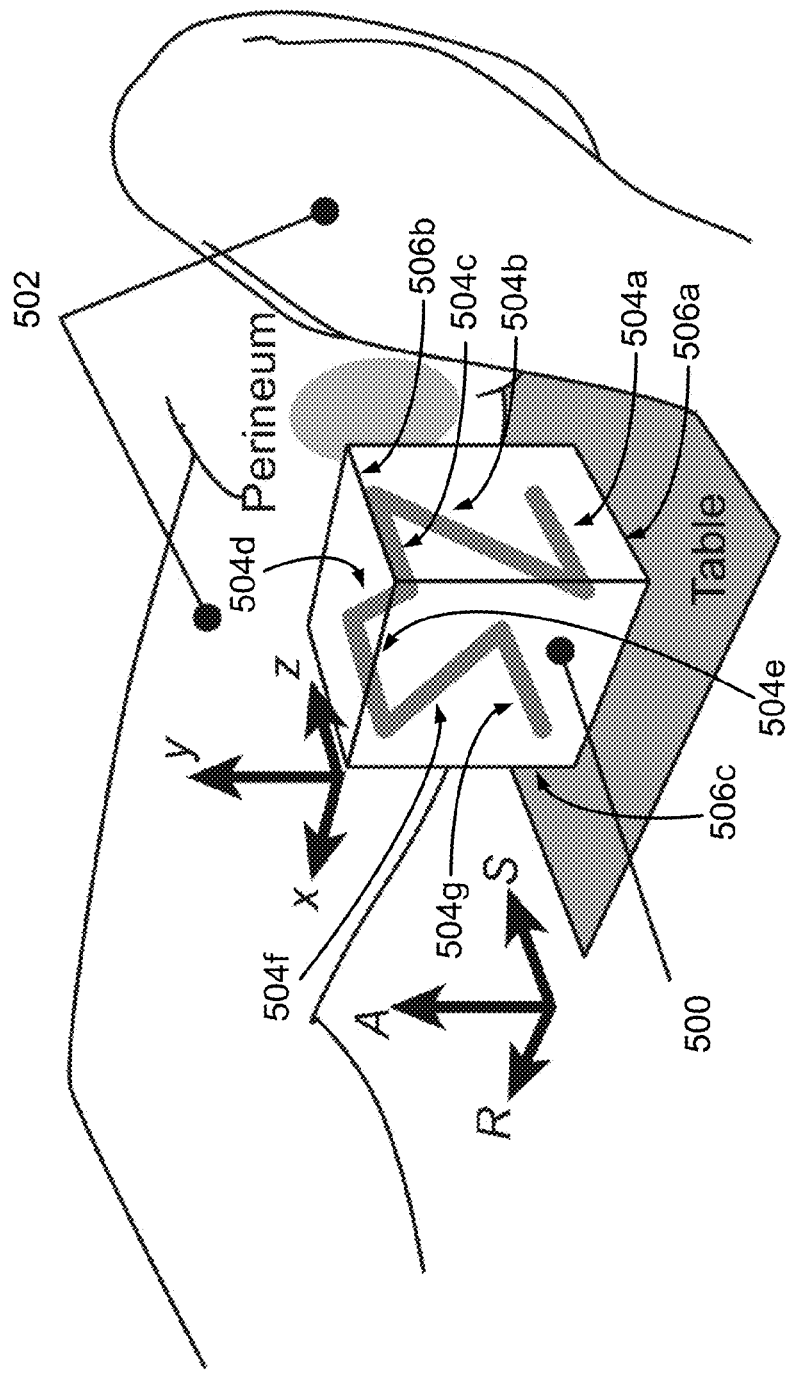
FIG. 5 is a is a perspective view of a fiducial marker frame arranged with respect to a patient in accordance with the present disclosure.

One non-limiting example of a fiducial frame is illustrated in FIG. 5. Particularly, a fiducial marker configuration can be constructed as a Z-frame 500 that is designed to be located proximate to a patient 502. Notably, though shown as straight lines that form a z-shape, this configuration is not required. The markers may be straight lines or curved. Furthermore, it is not necessary to have a large number of markers. The Z-frame 500, as illustrated, includes seven rigid cylindrical tubes that formed elongated fiducial markers 504a-504g. However, there may be less markers, such as three markers. The elongated markers may be formed by the cylindrical tubes with, for example, 7.5 mm inner diameter and 30 mm length that can be filled with a contrast agent, such as iodine for CT imaging and arranged relative to three adjacent faces 506a-506c of, for example, a 60 mm cube.

At process block 304, imaging data is acquired and, at process block 306, the images are analyzed to detect the markers. To distinguish the fiducial frame from other anatomical structures, at process block 306a, a line filter can applied to the image of the fiducial frame to highlight the lines that have the same width as the elongated markers. An example of a 3D multi-scale line filter is provided in Sato, Y., Nakajima, S., Shiraga, N., Atsumi, H., Yoshida, S., Koller, T., Gerig, G., Kikinis, R.: Three-dimensional multi-scale line filter for segmentation and visualization of curvilinear structures in medical images. Med Image Anal 2(2) (1998) 143-68, which is incorporated herein by reference in its entirety. The filter can target 3D lines of a specific width by $\sigma_f$, the standard deviation of the isotropic Gaussian function used to estimate the partial second derivatives. The filtered image is then segmented at process block 306b. For example, the images may be binarized with a threshold such that only the voxels within the line structures may be labeled '1', while the remaining voxels may be labeled '0'. The voxels within the lines are then relabeled so that each segment has a unique voxel value.

At process block 306c, each segment is examined with respect to a model. For example, if the volume in a given segment is within a pre-defined range [$V_{min}$; $V_{max}$], the length and width of the segment can be assessed by computing the principal eigenvector of the distribution of the voxels in the segment.

For example, the configuration of the fiducial frame can be modeled as a model line set $\{l_1^M, \ldots, l_{N_M}^M\}$ in the registration algorithm. Each line can be described by a pair of position and direction vectors, $p_i^M$ and $n_i^M$ ($i=1, \ldots, N^M$); those vectors represent the coordinates of a point on the line and the direction vector of the line defined in the fiducial frame coordinate system, respectively.

Figure 4:
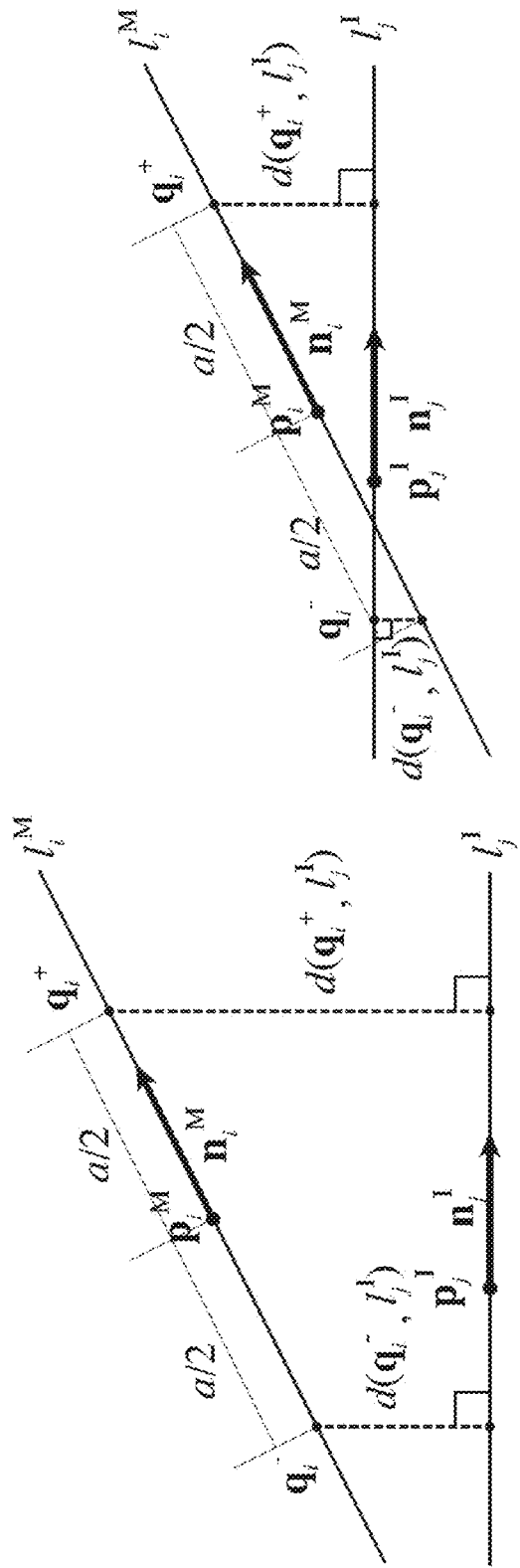
FIG. 4 is a graphic illustrating a process for registration of two line sets in accordance with the present disclosure.

The two line sets are registered at process block 308. That is, once the markers are identified as a line set, $\{l_1^I, \ldots, l_{n'}^I\}$ on the image(s), the line set in the model $\{l_1^M, \ldots, l_{n^M}^M\}$ is registered to $\{l_1^I, \ldots, l_{N^I}^I\}$. The challenge here is that the transformation that registers the model to the image cannot be determined analytically, because an one-to-one correspondence between $\{l_1^M, \ldots, l_{N^M}^M\}$ and $\{l_1^I, \ldots l_{N^I}^I\}$ has not been established. To address this challenge, the present disclosure provides an approach similar to an iterative closest line (ICL) process, such as described in Alshawa, M.: ICL: Iterative closest line a novel point cloud registration algorithm based on linear features. Ekscentar 10 (2007) 53-59, which is incorporated herein by reference in its entirety. The ICL is a point cloud registration algorithm alternative to the iterative closest points (ICP). However, whereas the ICP registers two point clouds by iteratively associating points in the two clouds by nearest-neighbor criteria, the ICL registers them by associating linear features extracted from the point clouds. Unlike ICL, the present disclosure can compute the translation and rotation at once rather than computing them separately. To achieve this, a distance function can be defined that becomes zero when two given lines match. That is, referring to FIG. 4, one can defined a distance function between one of the lines in the model of the fiducial frame, $l_i^M$, and one of the lines extracted from the image, $l_j^I$, using the distances from two points $q_i^-$ and $q_i^+$ on line $l_i^M$ to line $l_j^I$. Within this context, $q_i^-$ and $q_i^+$ are defined by point $p_i^M$, direction vector $v_i^M$ the distance to $p_i^M$, q/2. The distance function gives zero only if the two lines match. Although the distance function depends on how $p_i^M$ is chosen, it does not depend on the location of $p_j^I$ along line $l_j^I$. Therefore, the distance function is insensitive to translation along line $l_j^I$ during the registration process.

Thus, the segment is identified as an elongated marker if its length along the principal eigenvector is close to the physical length of the markers. Once the segment is identified as a marker, $l_j^I$, the centroid of the segment can be calculated as $p_j^I$, and the principal eigenvector as $n_j^I (j=1, \ldots, N^I)$.

The two points on line $l_i^M$ are defined by $q_i^+=p_i^M+an_i^M/2$ and $q_i^-=p_i^M-an_i^M/2$, where the distance between the two points is a. The distances from those points to line $l_j^I$ are:

$$d(q_i^+,l_j^I)=\|(q_i^++p_j^I-\{(q_i^+-p_j^I)\Box n_j^I\}n_j^I\|$$ Eqn. (3); and $$d(q_i^-,l_j^I)=\|(q_i^-+p_j^I-\{(q_i^--p_j^I)\Box n_j^I\}n_j^I\|$$ Eqn. (4).

If the error function for line $l_i^M$ and line $l_j^I$ is defined as:

$$E(l_i^M,l_j^I)=d(q_i^+,l_j^I)+d(q_i^-,l_j^I)$$ Eqn. (5);

the error function between line $l_i^M$ and the line set identified on the images, $L^I=\{l_1^I, \ldots, l_{N^I}^I\}$ can be defined as:

$$E(l_i^M, L^I) = \min_{j \in 1,\ldots,N^I} E(l_i^M, l_j^I).$$ Eqn. (6)

Finally, the linear transformation can computed by optimizing E using an iterative approach, such as in ICP, as indicated at decision block 310. Once the linear transformation is computed and the markers are matched to the model, at process block 312, an output report is generated. For example, in some instances, this report may be an indication of the position of the markers on the imaging data, as matched against the model. In other instances, the output may be a sets of registered images using the markers.

EXPERIMENTS

The performance of the above-described systems and methods were evaluated using the above-described Z-frame. The base of the Z-frame was fixed with a scale on the patient table of a 3 Tesla MRI scanner to give known translations and rotations to the Z-frame. The scale allowed the Z-frame to be placed at 0, 50, 100, 150, and 200 mm horizontally off the isocenter of the imaging bore, and tilted 0, 5, 10, 15, and 20 degrees horizontally from the B0 field. The accuracy of the Z-frame registration, was evaluated while translating the Z-frame along the Z-frame's X- and Y-axes and rotating around the X-, Y- and Z-axes (i.e., roll, pitch and yaw, respectively such as noted in FIG. 5). The translation along the Z-axis was not considered, since the scanner can position the subject to its isocenter by moving the table. For the acquisition of the 3D images, the 3D Fast Low Angle Shot (FLASH) imaging sequence was used (TR/TE: 12 ms/1.97 ms; acquisition matrix: 256×256; flip angle 45 degrees; field of view: 160 c 160 mm; slice thickness: 2 mm; receiver bandwidth: 400 Hz/pixel; number of averages: 3). For each translation and rotation, eight sets of 3D images were acquired. Traditional detection and registration methods were applied to compare against the detection and registration systems and methods of the present disclosure.

MRI data of the Z-frame was obtained during clinical MRI-guided prostate biopsies performed under a study protocol approved by the Institutional Review Board. Three-dimensional images of the Z-frame acquired at the beginning of each case were collected in 50 clinical cases, where the Z-frame was used to register the needle guide template. We performed automatic registration of the Z-frame using the above-described methods. The results were visually inspected by overlaying the Z-frame model on the MR images.

Results

Figures 6A, 6B:
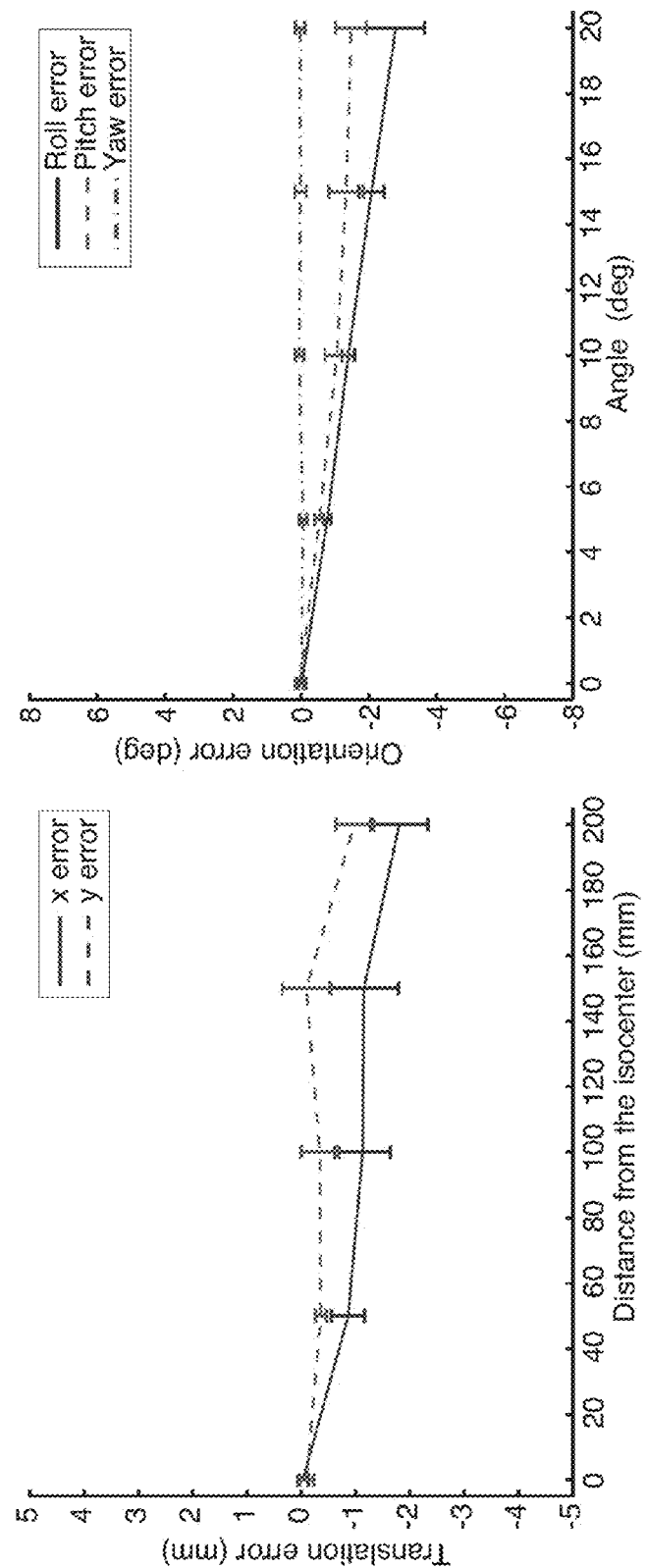
FIGS. 6A and 6B are graphs illustrating the mean and standard deviations of the translational registration errors when the fiducial frame is placed at 0, 50, 100, 150, and 200 mm horizontally off the isocenter and the rotational registration errors when it was tilted 0, 5, 10, 15, and 20 degrees around the X, Y, and Z axis of the frame from its original position.

The parameters for the multi-scale line filter were as follows: $\sigma_f=3.0$, $\alpha_1=0.5$, and $\alpha_2=2.0$. We used threshold for the Hessian matrix=13.0, $[V_{min}; V_{max}]=[300$ mm$^3$; 2500 mm$^3]$, and minimum length of principal axis=10 mm. Registration of the Z-frame on all MR images was successfully completed without tuning the parameters. FIGS. 6A and 6B show the errors between translations and rotations of the Z-frame estimated from the present registration method and measured on the scale. The average time for computation was 4.3 seconds per image. Table 1 shows a comparison between the registration accuracy of the present systems and methods and that of the existing algorithm. That is, Table 1 provides a comparison between the registration accuracy of a traditional method and the systems and method for the present disclosure using the Mann-Whitney U test.

TABLE 1

|  | X (mm) | Y (mm) | Roll (deg) | Pitch (deg) | Yaw (deg) |
| --- | --- | --- | --- | --- | --- |
| Original | −1.08 ± 0.80 | −1.44 ± 1.83 | −0.70 ± 0.97 | −1.55 ± 1.55 | 0.04 ± 0.05 |
| Proposed | −1.00 ± 0.73 | −0.38 ± 0.44 | −1.41 ± 1.06 | −0.87 ± 0.66 | 0.01 ± 0.13 |
| p-value | 0.5 | 0.005 | 0.01 | 0.1 | $9.0 \times 10^{-6}$ |

With respect to the clinical study, the same parameters were used in the clinical study. Visual inspection of the results showed that, the Z-frame was successfully registered in 98 percent of the cases. In one case, threshold values for minimum and maximum volume of markers had to be adjusted to achieve successful registration. The average computation time was 5.6 seconds.

Thus, the above-described systems and method provide a robust and automatic fiducial frame detection and registration system and method that can be applied to a variety of fiducial frame designs, imaging modalities, and clinical applications. The phantom study demonstrated that the proposed systems and methods are capable of registering the model of the fiducial frame to the MR images with an accuracy of 1:00 0:73 mm and 1:41 1:06 degrees. The clinical study demonstrated that the method was sufficiently robust to detect the fiducial frame with a success rate of 98 percent without any manual operation.

The use of elongated markers, for example, cylindrical markers, is advantageous the described systems and methods. In some cases it may be that the automatic extraction of 3D linear features from cylindrical markers on the input image is more robust than that of spherical markers or sections of cylindrical markers because the Hessian matrix can selectively highlight the linear structures with a specific width, and once the linear structures are extracted, several criteria, such as volume and size in primary and secondary axes, can be applied to filter out unwanted structures.

By using elongated markers that are treated as lines instead of points in the present disclosure, the method is less prone to detection error due to image defects than the other approaches that rely on simple thresholding. In practice, signal defects are often caused by bubbles in capsules of liquid-based MR-visible markers or other defects in other frames/systems. However, the signal defects can still impact the registration accuracy in our approach, because a line is identified as the eigenvectors of the voxel distribution in the segmented markers. To this point, Krieger, A., lordachita, I., Guion, P., Singh, A. K., Kaushal, A., Menard, C., Pinto, P. A., Camphausen, K., Fichtinger, G., Whitcomb, L. L.: An MRI-compatible robotic system with hybrid tracking for MRI-guided prostate intervention. IEEE Trans Biomed Eng 58(11) (2011) 3049-60 proposed the use of template matching to minimize the effect of bubbles, which is incorporated herein by reference in its entirety.

The proposed method provides several advantages over other methods for fully ostensibly automated device-to-image registration. First, can be designed to only rely on passive markers and does not require any embedded coil or MR pulse sequence to enhance the signal from the markers. Second, the algorithm does not assume any particular frame design for automatic detection and registration. The only requirement for the fiducial frame design is the use of multiple elongated markers, preferably, arranged asymmetrically. Such arrangement allows automatic detection and registration of a wide variety of needle guide devices. Third, the algorithm does not require any modification of its implementation in order to be adapted to a particular fiducial frame design. It only requires modifying a model of the frame and parameters, which can be provided as a configuration file. Therefore, even developers who are not specialized in image processing can design and implement device-to-image registration. Those advantages help developers to design needle guide devices with less effort and fewer constraints.

The present invention has been described in terms of one or more preferred embodiments, and it should be appreciated that many equivalents, alternatives, variations, and modifications, aside from those expressly stated, are possible and within the scope of the invention.

The invention claimed is:

1. A system comprising:
a computer system including a non-transitive, computer-readable storage medium having stored thereon a program that causes the computer system to:
   access image data illustrating a subject and plurality of elongated fiducial markers arranged in a rotationally asymmetric orientation;
   analyze the image data to detect the elongated fiducial markers by applying a line filter to treat the elongated fiducial markers as lines within the image data;
   enhance a contrast of the elongated fiducial markers within the image data;
   match the enhanced contrast of the elongated fiducial markers within the image data to a model of the elongated fiducial markers;
   register the image data with a coordinate system based on the matching of the enhanced contrast of the elongated fiducial markers to the model of the elongated fiducial markers; and
   generate a report indicating at least the registered image data.

2. The system of claim 1 wherein the line filter includes a multi-scale line filter.

3. The system of claim 1 wherein the image data includes data from at least three asymmetrically oriented elongated fiducial markers.

4. The system of claim 1 wherein the image data includes three-dimensional (3D) image data.

5. The system of claim 1 wherein the computer system is further caused to iteratively determine a correspondence of the elongated fiducial markers to the model to perform the matching.

6. The system of claim 1 wherein the image data includes at least one of magnetic resonance image data and computed tomography image data.

7. The system of claim 1 wherein the report includes a plan for a therapeutic treatment of the subject.

8. A method for automatically registering medical images with an image coordinate system, the method comprising steps of:
a) positioning a fiducial frame having a plurality of elongated fiducial markers arranged rotationally asymmetric and proximate to a subject;
b) acquiring, with a medical imaging system, image data of the subject and fiducial frame;
c) applying a line filter that treats the elongated fiducial markers as lines within the image data;
d) distinguishing the elongated fiducial markers within the image data;
e) matching the elongated fiducial markers within the image data to a model of the elongated fiducial markers;
f) registering the image data with a coordinate system based on the matching of the elongated fiducial markers to the model of the elongated fiducial markers; and
g) generating a report indicating at least the registered image data.

9. The method of claim 8 further comprising registering the registered image with at least one of a surgical and a therapeutic plan using the report.

10. The method of claim 8 further comprising apply a multi-scale line filter in step c).

11. The method of claim 8 wherein step a) includes arranging at least three asymmetrically oriented elongated fiducial markers proximate to the subject.

12. The method of claim 8 wherein step b) includes acquiring three-dimensional (3D) image data.

13. The method of claim 8 wherein step e) includes iteratively determining a correspondence of the elongated fiducial markers to the model.

14. The method of claim 8 wherein the medical imaging system includes at least one of magnetic resonance system and a computed tomography system.

15. The method of claim 8 wherein steps c) through g) are performed automatically by a computer system that includes a non-transitive, computer-readable storage medium having stored thereon a program that causes the computer system to carry out steps c) through g) automatically.

16. The method of claim 8 wherein the fiducial frame is a free-standing system and the elongated fiducial markers are arranged to form opposing z-shapes connected by an elongated fiducial marker.

17. A system for automatically registering medical images with an image coordinate system, the system comprising:
a fiducial frame having a plurality of elongated fiducial markers arranged rotationally asymmetric within the fiducial frame;
an imaging system configured to acquire image data from the fiducial frame and a subject located proximate to the fiducial frame;
a computer system including a non-transitive, computer-readable storage medium having stored thereon a program that causes the computer system to:
access the image data of the subject and the fiducial frame;
analyze the image data to detect the elongated fiducial markers by applying a line filter to treat the elongated fiducial markers as lines within the image data;
match the elongated fiducial markers detected within the image data to a model of the elongated fiducial markers;
register the image data with a coordinate system based on the matching of the enhanced contrast of the elongated fiducial markers to the model of the elongated fiducial markers; and
generate a report indicating at least the registered image data.

18. The system of claim 17 wherein the line filter includes a multi-scale line filter.

19. The system of claim 17 wherein the medical imaging data includes three-dimensional (3D) image data.

20. The system of claim 17 wherein the computer system is further caused to iteratively determine a correspondence of the elongated fiducial markers to the model to perform the match.

* * * * *

UNITED STATES PATENT AND TRADEMARK OFFICE
CERTIFICATE OF CORRECTION

PATENT NO. : 9,993,211 B2
APPLICATION NO. : 14/491872
DATED : June 12, 2018
INVENTOR(S) : Junichi Tokuda et al.

It is certified that error appears in the above-identified patent and that said Letters Patent is hereby corrected as shown below:

In the Specification

Column 8, Line 58, "$l_{NM}{}^{M}$" should be --$l^M_{NM}$--.

Column 8, Line 65, "$l_{n1}{}^{I}$" should be --$l^I_{N1}$--.

Column 8, Line 66, "$l_{nM}{}^{M}$" should be --$l^M_{NM}$--.

Column 8, Line 67, "$l_{n1}{}^{I}$" should be --$l^I_{N1}$--.

Column 9, Line 3, "$l_{nM}{}^{M}$" should be --$l^M_{NM}$--.

Column 9, Line 3, "$l_{n1}{}^{I}$" should be --$l^I_{N1}$--.

Column 9, Line 48, "$l_{n1}{}^{I}$" should be --$l^I_{N1}$--.

Signed and Sealed this
Fifth Day of March, 2019

Andrei Iancu
*Director of the United States Patent and Trademark Office*